US006473172B1

(12) United States Patent
Pelmulder

(10) Patent No.: US 6,473,172 B1
(45) Date of Patent: Oct. 29, 2002

(54) FLOW CELL AND METHOD OF OPERATING THEREFOR

(75) Inventor: John P. Pelmulder, Chatsworth, CA (US)

(73) Assignee: International Remote Imaging Systems, Inc., Chatsworth, CA (US)

( * ) Notice: Subject to any disclaimer, the term of this patent is extended or adjusted under 35 U.S.C. 154(b) by 0 days.

(21) Appl. No.: 09/665,387

(22) Filed: Sep. 20, 2000

(51) Int. Cl.$^7$ .................................................. G01N 1/10

(52) U.S. Cl. ........................................ 356/246; 356/336

(58) Field of Search ......................... 356/246, 73, 335, 356/336, 337

(56) References Cited

U.S. PATENT DOCUMENTS

| | | | | |
|---|---|---|---|---|
| 2,480,312 A | | 8/1949 | Wolf | 235/92 |
| 2,791,150 A | | 5/1957 | Stevens | 235/92 |
| 3,390,229 A | | 6/1968 | Williams | 356/23 |
| 3,560,754 A | | 2/1971 | Kamentsky | 250/218 |
| 3,819,270 A | | 6/1974 | Hirschfield | 356/39 |
| 3,976,862 A | | 8/1976 | Curbelo | 235/151.34 |
| RE29,141 E | | 2/1977 | Hogg | 356/36 |
| 4,075,462 A | | 2/1978 | Rowe | 235/92 |
| 4,097,845 A | | 6/1978 | Bacus | 356/39 |
| 4,175,860 A | | 11/1979 | Bacus | 356/39 |
| 4,199,748 A | | 4/1980 | Bacus | 340/146.3 |
| 4,338,024 A | | 7/1982 | Bolz et al. | 356/23 |
| 5,106,187 A | * | 4/1992 | Bezanson | 356/73 |
| 5,162,863 A | * | 11/1992 | Ito | 356/73 |

FOREIGN PATENT DOCUMENTS

| | | |
|---|---|---|
| DE | 26 56 263 A1 | 8/1978 |
| GB | 1 557 691 | 12/1979 |
| JP | 51-95884 | 8/1976 |

OTHER PUBLICATIONS

Edited by Melamed et al.; *Flow Cytomerty and Sorting*, 1979.
Internal Calibration to Absolute Values in Flowthrough Particle Size Analysis, W.G. Eisert and M. Nezel, Rev. Sci. Instrum. 49(12), Dec. 1978.
Uniform Lateral Orientation, Caused by Flow Forces, of Flat Particles in Flow–Through Systems, V. Kachel, E. Kordwig, and E. Glossner, Journal of Histochemistry Society, Inc., vol. 25, No. 7, pp. 774–780, 1977.
Imaging in Flows, D.B. Kay, J.L. Cambier and L.L. Wheeless, Journal of Histochemistry and Cytochemistry, vol. 27, No. 1, pp. 329–334, 1979.
Fast Imaging in Flow, V. Kachel, G. Benker, K. Lichtnau, G. Valet and E. Glossner, Journal of Histochemistry and Cytochemistry, vol. 27, No. 1, Jan. 1979.

* cited by examiner

*Primary Examiner*—Frank G. Font
*Assistant Examiner*—Roy M Punnoose
(74) *Attorney, Agent, or Firm*—Gray Cary Ware & Freidenrich LLP

(57) ABSTRACT

A flow cell for analysis of particles in a sample fluid buffered by sheath fluid has a sample inlet to receive the sample fluid and a sheath inlet for receiving the sheath fluid. The sample fluid flows in a flow direction from the sample inlet past an examination region to an outlet. A flow distributor is positioned between the sheath inlet and the examination region for distributing the sheath fluid ranging in a first direction substantially paralleled to the flow direction to the second direction substantially perpendicular to the flow direction. The distribution of the sheath fluid at the output of the distributor is vortex-free over a wide range of input directions and input chamber geometries. It eliminates the creation of vortices that could cause mixing and instability of the sample fluid in the examination area and allows greater freedom in shaping the fluid system for optimal hydrodynamic focusing.

17 Claims, 3 Drawing Sheets

FLOW CELL AND METHOD OF OPERATING THEREFOR

TECHNICAL FIELD

The present invention relates to an improved flow cell for analysis of particles in a sample fluid, which is buffered by a sheath fluid. More particularly, the present invention relates to a flow distributor for distributing the sheath fluid ranging in a first direction substantially paralleled to flow direction of flow of the sample fluid to a second direction substantially perpendicular to the flow direction of the sample fluid. The present invention also relates to a method of operating such a flow cell.

BACKGROUND OF THE INVENTION

Flow cells for analyzing particles flowing in a sample fluid buffered by sheath fluid are well known in the art. See, for example, U.S. Pat. No. 4,338,024 assigned to the assignee of the present application.

Typically, flow cells of the type described hereinabove and hereinafter, are used in analytical instruments to position and present a sample fluid containing particles of interest for analysis. The more accurately that the sample fluid is positioned, the better the analysis of the particles therein can be made. Typically, the sample fluid and a sheath fluid that buffers the sample fluid are made to flow together from a large entry chamber into a small cross sectional examination area or region. The transition from the inlet or entry chambers to the examination region forms a hydrodynamic lens that squeezes both the sample fluid and the sheath fluid proportionally into the smaller space. Where the particles of interest are microscopic particles, the resulting cross-sectional space occupied by the sample fluid must position the particles within the depth of field of an instrument, such as an optical system or a laser system, to obtain the best analytical information. For the best hydrodynamic focus, a large area of sheath flow must envelop the small area of sample fluid without any swirling or vortices.

SUMMARY OF THE INVENTION

Accordingly, in the present invention, a flow cell for analysis of particles in a sample fluid, which is buffered by sheath fluid, has a flow chamber with a sample inlet for receiving the sample fluid and a sheath inlet for receiving the sheath fluid. The flow cell also has an outlet for the sample fluid and the sheath fluid with the flow cell shaped to convey the sample fluid in a flow direction from the sample inlet past an examination region to examine the particles of the sample fluid to the outlet. The flow cell also comprises a flow distributor, which is positioned between the sheath inlet and the examination region for distributing the sheath fluid ranging in a first direction substantially paralleled to the flow direction to a second direction substantially perpendicular to the flow direction.

The present invention also relates to a method of flowing a sheath fluid and a sample fluid in the flow cell past an examination area for analysis. The sample fluid is flowed in a flow direction from a sample inlet past the examination area to an outlet. The sheath fluid is flowed into the flow cell. The sheath fluid is then distributed by a flow distributor in a plurality of directions ranging in a first direction, which is substantially paralleled to the flow direction to a second direction which is substantially perpendicular to the flow direction prior to the sheath fluid flowing into the examination area. The sheath fluids with the sample fluid from the examination area are then flowed to outlet.

DETAILED DESCRIPTION OF DRAWINGS

Figure 1:
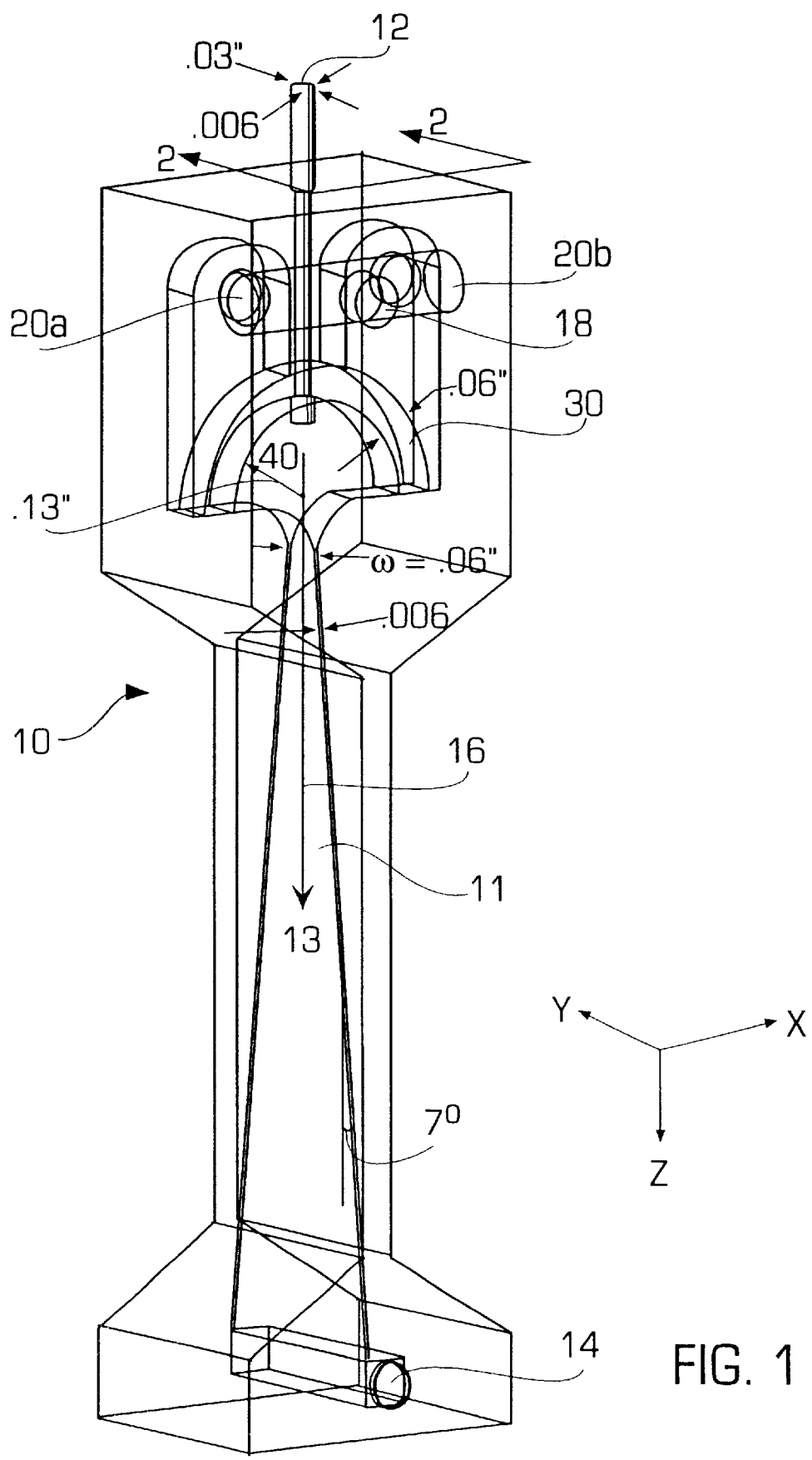
FIG. 1 is a perspective view of a preferred embodiment of the flow cell of the present invention.

Referring to FIG. 1 there is shown a perspective view of an improved flow cell 10 of the present invention. The flow cell 10 has a sample inlet 12 for receiving the sample fluid which as particles of interest therein. The sample inlet 12 receives the sample fluid and flows the sample fluid in a flow direction 13 past an examination area 16 to an outlet 14. The sample fluid is flowed past the examination area 16, which is substantially coplanar with the plane 11 of flow of the sample fluid.

The flow cell 10 also has a sheath inlet 18, which receives sheath fluid. The sheath inlet 18 is positioned substantially parallel to the plane 11. However, as will be seen, with the present invention, the geometry of the position of the sheath inlet 18 or the geometry of the position of the sample inlet 12 relative to the plane 11 is immaterial. The sheath fluid once it enters into the flow cell 10 is distributed to two inlets 20A and 20B each substantially to one side and the other side of the plane 11. The sheath fluid then flows into an arch shaped porous flow distributor 30. As shown in FIG. 1, the flow cell 10 is positioned substantially vertically and thus the sheath fluid would flow in a downward direction. However, the flow cell 10 can also be positioned horizontally and the pressure flow of the sheath fluid would also push the sheath fluid past the inlets 20A and 20B to impinge on the flow distributor 30.

Figure 2:
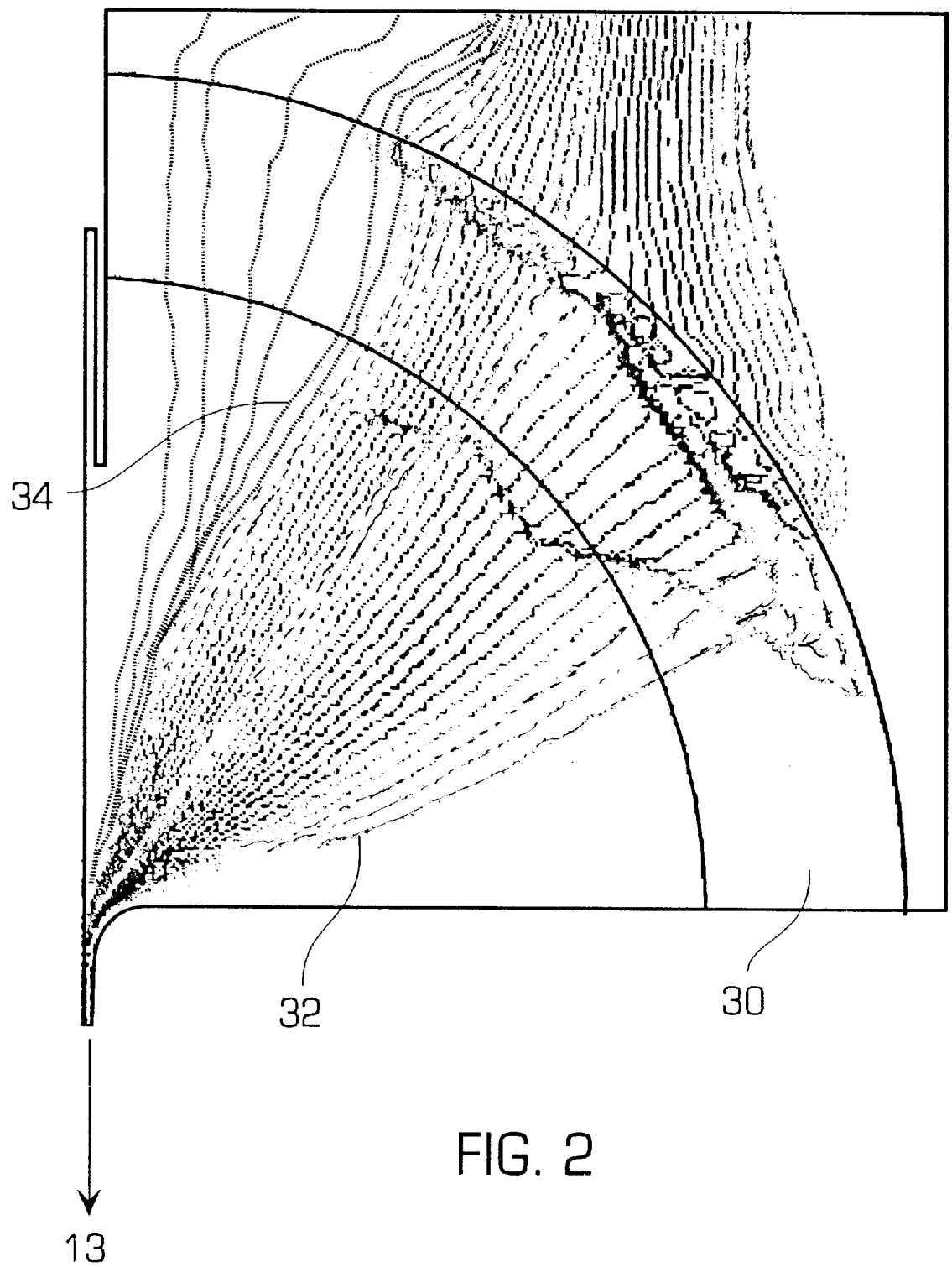
FIG. 2 is a cross-sectional view of a portion of the flow cell shown in FIG. 1, taken along the line 2—2 showing the sheath flow predicted by a computational fluid dynamics model.

The flow distributor 30 is positioned between the sheath inlets 20A and 20B and the examination area 16 to distribute the sheath fluid ranging in a first direction 34, which is substantially parallel to the flow direction 13 to a second direction 32 which is substantially perpendicular to the flow direction 13, as can be seen in FIG. 2. The action of the sheath fluid flowing in the second direction 32, which is substantially perpendicular to the flow direction 13 on both sides of the flow direction 13, forces the sample fluid to be confined in a narrow, well defined plane which would be within the depth of field of the examination region 16. This is shown as the direction X in FIG. 1. The flow action of the sheath fluid in the Z direction caused by the distribution of the porous distributor 30 on both side of the sample fluid, causes the fluid sample 30 to be buffered between the two layers of the sheath fluid as it flows 34 past the examination area 16.

Finally, because the width (Y direction) of the sheath fluid is as wide as the width of the examination area W which is perpendicular to the flow direction 13, and because the width of the sample fluid is narrower than the width W of the examination region, the sample fluid is constrained to lie within the dimensions of the Y direction into which it flows into the sample inlet 12. As a result of this hydrodynamic force, the sample fluid is constrained to lie within a certain range in the Y direction, is constrained to lie in a certain plane in the YZ direction by the force acting in the X direction, and is buffered by the sheath fluid on both sides of the X direction as it flows passed the examination area 16 in the Z direction.

The function of the porous flow distributor 30 is to provide a uniform, lamina, slow flow of sheath fluid into the entry chamber over a large area. In a preferred embodiment, the porous flow distributor 30 is an arch shaped filter, which creates radial flow of the sheath fluid towards the entrance into the examination region 16 ranging from the first direction 34 which is parallel to the flow direction 13 to the second direction 32 which is substantially perpendicular to flow direction 13. This creates a planar distribution of the sample fluid 12 in an extremely thin layer in the examination region 16. Further, in the preferred embodiment, the entry chamber 40 is wide in the same axes that the analysis region is narrow. This causes the sample fluid to be squeezed into the minimum thickness region surrounded by the sheath fluid. The entry chamber 40 is of roughly the same width as the entrance to the examination region 16 in the other axes where no squeezing of the specimen stream is needed.

As previously stated, the flow cell 10 shown in FIG. 1 is positioned vertically with the sample fluid flown from sample inlet 12 downward to an outlet 14. The flow direction of course can also be reversed, in the preferred embodiment, with the benefit that if the flow direction were from a sample inlet 12 upward to an outlet 14, continuous purging of air bubbles in the system would occur as it operates.

In the preferred embodiment, the porous flow distributor 30 is made of a filter material, from Porex Technologies (X-4897) which is a high density polyethylene plastic having 15–40 um pores with the pores constituting 40–50% by volume. In the preferred embodiment, the dimensions of the porous flow distributor 30 and of the flow cell 10 are as shown in FIG. 1.

Figure 3:
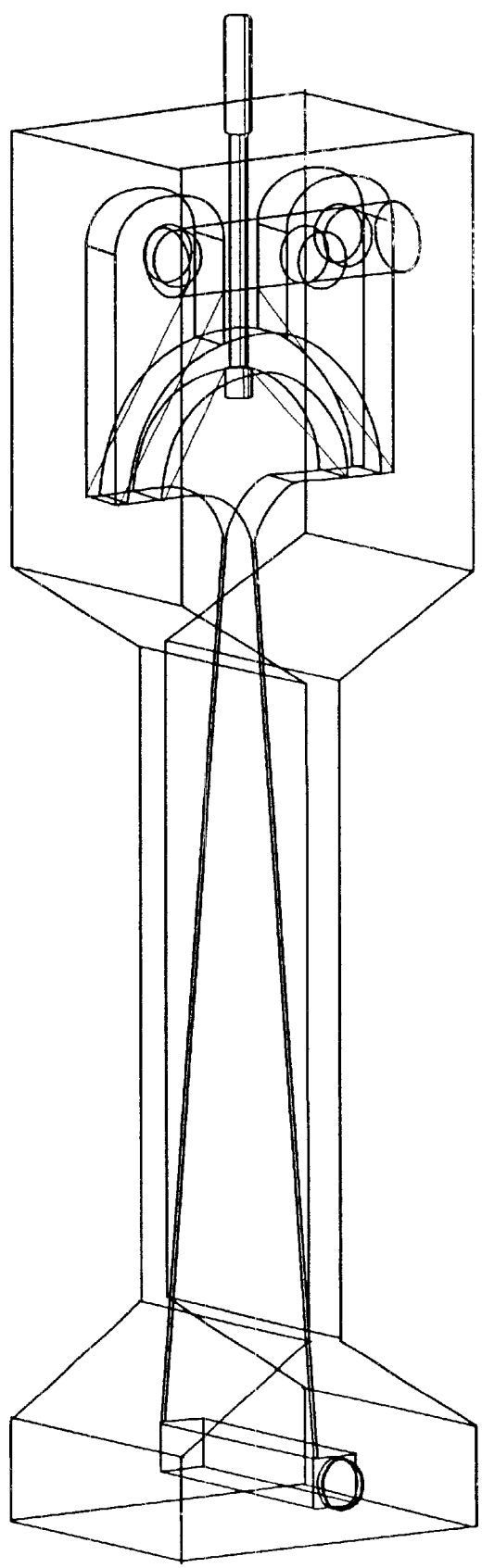
FIG. 3 is a perspective view of another embodiment of the flow cell of the present invention.

Referring to FIG. 3, there is shown a perspective view of another embodiment of the improved flow cell 10 of the present invention. In this embodiment, the flow distributor is substantially incline shaped flowing sheath fluid to the examination region.

There are many advantages to the apparatus and method of the present invention. Through the flow cell 10 of the present invention, a thinner sample fluid can be delivered to the examination region 16 without mixing or instability and can be accomplished even though the cross-sectional area of the examination region 16 can be made larger to reduce the danger of clogging. However, without the porous flow distributor 30 a similarly shaped chamber would have vortices that cause mixing and unstable positioning of the sample fluid. The introduction of the porous flow distributor 30 allows greater freedom in shaping the fluid system for optimum hydrodynamic focusing without the limitations caused by flow separation.

Thus, the present invention includes a physical element, such as porous flow distributor, positioned between the sheath inlet and the examination area to produce proper sheath flow characteristics regardless of the sheath inlet geometry and the geometry of the sheath inlet chamber. Although, a passive flow distributor is shown and described, it will be clear to one having ordinary skill in the art that an active element for redirecting the flow of the sheath fluid can be equally applied. See, for example, MEMS type devices described at http://ho.seas.ucla.edu/mainflash.html. Further, although the invention has been described with respect to redirecting the flow of sheath fluid form its inlet to an examination area in a planar flow cell, the present invention can also be used in a cylindrically shaped flow cell.

What is claimed is:

1. A flow cell for analysis of particles in a sample fluid, buffered by a sheath fluid, said flow cell comprising a sample inlet for receiving said sample fluid, a sheath inlet for receiving said sheath fluid and an outlet for said sample fluid and said sheath fluid; said flow cell shaped to convey said sample fluid in a flow direction from said sample inlet past an examination region to examine particles of said sample fluid, to said outlet; and a flow distributor positioned between said sheath inlet and said examination region for distributing said sheath fluid ranging in a first direction substantially parallel to said flow direction to a second direction substantially perpendicular to said flow direction.

2. The flow cell of claim 1 wherein said flow distributor is an active element.

3. The flow cell of claim 1 wherein said flow distributor is a passive element.

4. The flow cell of claim 3 wherein said flow distributor is a porous flow distributor.

5. The flow cell of claim 4 wherein said flow cell is substantially cylindrically shaped.

6. The flow cell of claim 4 wherein said flow cell is substantially planarly shaped.

7. The flow cell of claim 6 wherein said examination region has a width substantially perpendicular to said flow direction and said examination region is substantially planar in a plane and wherein said sample inlet is substantially co-planar with said plane.

8. The flow cell of claim 7 wherein said flow cell comprises two sheath inlets, one inlet to one side of said plane and another inlet on a side opposite said one side of said plane.

9. The flow cell of claim 8 wherein said sample inlet conveys said sample fluid across a first width less than said width of said examinations region, and wherein each of said two sheath inlets convey said sheath fluid across a second width substantially equal to said width of said examination region.

10. The flow cell of claim 9 wherein said distributor is substantially inclined from said sheath inlet to said examination region.

11. The flow cell of claim 9 wherein said flow distributor is arch shaped with a curvature curving to said sheath inlet from said examination region.

12. The flow cell of claim 11 wherein said flow distributor is made from porous plastic.

13. The flow cell of claim 12 wherein said sheath inlet is substantially perpendicular to said plane.

14. A method of flowing a sheath fluid and a sample fluid in a flow cell, having an examination area for analysis, said method comprising:

flowing said sample fluid in a flow direction from a sample inlet, past said examination area, to an outlet; and flowing said sheath fluid into said flow cell;

distributing said sheath fluid by a flow distributor in a plurality of directions ranging in a first directions substantially parallel to said flow direction to a second direction substantially perpendicular to said flow direction, prior to said sheath fluid flowing into said examination area; and flowing said sheath fluid with said sample fluid in said examination area to said outlet.

15. The method of claim 14 wherein said examination area lies substantially in a plane, and wherein said distributing step distributes said sheath fluid in two streams such that said plane lies between said two streams.

16. The method of claim 15 wherein said examination area has a width perpendicular to said flow direction and wherein said step for flowing said sample fluid flows said sample fluid in a first width less than said width of said examination area.

17. The method of claim 16 wherein said sheath fluid is distributed across the width of said examination area.

* * * * *